United States Patent [19]

Rodkey et al.

[11] Patent Number: 4,963,236

[45] Date of Patent: Oct. 16, 1990

[54] APPARATUS AND METHODS FOR ISOELECTRIC FOCUSING

[75] Inventors: L. Scott Rodkey; G. David Huff, both of Houston, Tex.

[73] Assignees: Ampholife Technologies; The Board of Regents University of Texas System, both of Houston, Tex.

[21] Appl. No.: 320,725

[22] Filed: Mar. 8, 1989

[51] Int. Cl.$^5$ .............................................. G01N 27/26
[52] U.S. Cl. ............................... 204/183.2; 204/299 R
[58] Field of Search .................................... 204/299 T

[56] References Cited

U.S. PATENT DOCUMENTS

| | | | |
|---|---|---|---|
| 2,878,178 | 3/1959 | Bier | 204/180 |
| 3,079,318 | 2/1963 | Bier | 204/180 |
| 3,657,106 | 4/1972 | Smith | 204/301 |
| 3,677,923 | 7/1972 | Bier | 204/180 |
| 3,686,089 | 8/1972 | Korngold et al. | 204/180 |
| 3,751,356 | 8/1973 | Takeya et al. | 204/299 |
| 3,788,959 | 1/1974 | Smith | 204/180 |
| 3,901,780 | 8/1975 | Denckla | 204/180 |
| 3,915,839 | 10/1975 | Rilbe et al. | 204/299 |
| 3,919,065 | 11/1975 | Heden | 204/180 |
| 3,951,777 | 4/1976 | Denckla | 204/299 |
| 3,962,058 | 6/1976 | Denckla | 204/180 |
| 3,972,791 | 8/1976 | Stern | 204/180 |
| 3,989,613 | 11/1076 | Gritzner | 204/180 |
| 4,040,940 | 8/1977 | Bier | 204/299 |
| 4,043,896 | 8/1977 | Ahlgren | 204/301 |
| 4,088,561 | 5/1978 | Anderson | 204/299 |
| 4,130,470 | 12/1978 | Rosengren et al. | 204/180 |
| 4,217,193 | 8/1980 | Rilbe | 204/180 |
| 4,234,404 | 11/1980 | Satoh | 204/299 |
| 4,243,507 | 1/1981 | Martin et al. | 204/301 |

(List continued on next page.)

OTHER PUBLICATIONS

Bier, M., "Forced-Flow Electrophoresis and its Biomedical Applications", Membrane Process for Industry-Proceedings of the Symposium (May 19-20, 1966), pp. 218-233.

(List continued on next page.)

Primary Examiner—John F. Niebling
Assistant Examiner—Isabelle Rodriguez
Attorney, Agent, or Firm—Workman, Nydegger & Jensen

[57] ABSTRACT

The present invention includes novel apparatus and methods for isoelectric focusing of amphoteric substances within fluids containing carrier ampholytes. The present invention utilizes multichannel recycling isoelectric focusing techniques which eliminate mixing of fluid which passes through the isoelectric focusing cell with the original crude fluid sample. Mixing is avoided by preferably using a dual reservoir system and alternating the fluid flow into and out of each reservoir after each pass through the isoelectric focusing cell. Fluid flow is alternated into and out of each reservoir of each reservoir pair through use of reservoir inlet and outlet valves. The reservoir inlet and outlet valves preferably operate in response to the fluid level within the reservoir supplying fluid to the isoelectric focusing cell. When the reservoir empties the corresponding reservoir outlet valve automatically engages to stop fluid flow from the empty reservoir and to start fluid flow from the full reservoir. Near instantaneously therewith, the reservoir inlet valve engages to stop fluid flow into the full reservoir and to start fluid flow into the empty reservoir.

The isoelectric focusing cell preferably has a plurality of inlet ports and a plurality of corresponding outlet ports. The inlet and outlet ports permit fluid to flow into and out of the isoelectric focusing cell along discrete channels. Each inlet and outlet port is then coupled to a pair of the alternating reservoirs.

The apparatus within the scope of the present invention preferably includes a heat exchanger for removing heat generated by the isoelectric focusing cell. The heat exchanger is preferably coupled directly to the isoelectric focusing cell thereby permitting greater power input to the focusing cell which results in rapid focusing of both the carrier ampholytes and the fluid sample.

74 Claims, 5 Drawing Sheets

U.S. PATENT DOCUMENTS

| | | | |
|---|---|---|---|
| 4,289,596 | 9/1981 | Satoh | 204/180 |
| 4,362,612 | 12/1982 | Bier | 204/299 R |
| 4,385,974 | 5/1983 | Shevitz | 204/180 |
| 4,396,477 | 8/1983 | Jain | 204/180 |
| 4,401,538 | 8/1983 | Hausfeld | 204/180 |
| 4,416,761 | 11/1983 | Brown et al. | 294/299 |
| 4,441,978 | 4/1984 | Jain | 204/301 |
| 4,484,141 | 11/1984 | Cook et al. | 324/464 |
| 4,495,279 | 1/1985 | Karpetsky et al. | 435/6 |
| 4,533,447 | 8/1985 | Meldon | 204/181.4 |
| 4,588,492 | 5/1986 | Bier | 204/301 |
| 4,670,119 | 6/1987 | Hurd | 204/183.2 |
| 4,673,483 | 6/1987 | Mandle | 204/301 |

OTHER PUBLICATIONS

Bier, M. et al., "New Developments in Isoelectric Focusing," Peptides-Structure and Biological Function, Proceedings of Sixth American Peptide Symposium, 1979, pp. 79-89.

Fawcett, John S., "Continuous-Flow Isoelectric Focusing and Isotachophoresis", Annals New York Academy of Sciences, pp. 112-126.

Fawcett, John S.,-"Continuous-Flow Isoelectric Focusing," Isoelectric Focusing, N. Catsimpoolas ed., Chapter 7 (1976), pp. 173-208.

Kolin, Alexander, "Isoelectric Focusing", Isoelectric Focusing, N. Catsimpoolas ed., Chapter 1 (1976), pp. 1-10.

Martin, A. J. P., et al., "New Apparatus for Isoelectric Focusing," Journal of Chromatography, vol. 159 (1978), pp. 101-110.

Nagabhushan, T. L. et al., "Application of Recycling Isoelectric Focusing for Purification of Recombinant Human Leukocyte Interferons," Electrophoresis 7 (1986), pp. 552-557.

Righetti, P. G. et al., "Theory and Fundamental Aspects of Isoelectric Focusing," Isoelectric Focusing, Chapter 1 (1976), pp. 341-376.

Rilbe, Harry, "Theoretical Aspects of Steady-State Isoelectric Focusing," Isoelectric Focusing, N. Catsimpoolas ed., Chapter 2 (1976), pp. 13-52.

Vesterberg, Olof, "The Carrier Ampholytes," Isoelectric Focusing, N. Catsimpoolas ed., Chapter 3 (1976), pp. 53-76.

APPARATUS AND METHODS FOR ISOELECTRIC FOCUSING

BACKGROUND

1. The Field of the Invention

The present invention relates to methods and apparatus for the isoelectric focusing of amphoteric substances. More particularly, the present invention is directed to the techniques for separating biological materials through the use of isoelectric focusing processes which enhance the separation characteristics of amphoteric biological substances and provide for efficient removal of heat generated during the isoelectric focusing process.

2. The Background of the Invention

Numerous areas of modern biology and genetic engineering depend on the availability of large quantities of high purity proteins. Currently available methods of protein purification include many kinds of chromatographic and electrophoretic techniques. Among these techniques, isoelectric focusing (hereinafter "IEF") has many attractive features.

The principle of IEF is based on the fact that certain biological materials (such as proteins, peptides, nucleic acids, and viruses) and even some living cells are amphoteric in nature—i.e., they are positively charged in an acidic media and negatively charged in a basic media. At a particular pH value, called the isoelectric point (hereinafter "pI"), these biomaterials will have a zero net charge.

Being charged in a pH gradient, the biomaterials migrate under the influence of an electric field until they reach the pH of their isoelectric point. At the isoelectric point, by virtue of their zero net charge, the biomaterials are not influenced by the electric field. Diffusion of "focused" biomaterials away from their pI will cause them to once again become charged, whereby they will electrophoretically migrate back to their pI. Thus, the biomaterials focus into narrow zones (defined by the pH of the medium and the electric field applied) from which the biomaterials can be selectively separated.

In one known method of isoelectric focusing, the pH gradient is established by the introduction of carrier ampholytes into the electric field. "Carrier ampholytes" are defined as ampholytes of relatively low molecular weight having conductance as well as buffer capacity, in the isoelectric state. Mixtures of synthetic polyaminopolycarboxylic acids have been used as carrier ampholytes.

In order to establish suitable pH gradients for IEF, it is necessary to have access to a great number of carrier ampholytes with isoelectric points well distributed along the pH scale. A commercial mixture of such amphoteric substances (called "Ampholine") is available from LKB Produkter AB, a Swedish Company. Ampholine is thought to be principally composed of polyaminopolycarboxylic acid molecules made by reacting polyamines with acrylic acid.

By manipulating the pH range of the carrier ampholytes, isoelectric focusing has the potential for high resolving power. However, the potential of isoelectric focusing as a means for separating amphoteric substances has not been realized because of the time necessary and the quality of separation of prior art processes.

Since acids are attracted to the anode of the electric field and bases to the cathode during electrolysis, an increasing pH gradient from the anode to the cathode will develop in a convection free electrolytic conductor. The success of isoelectric focusing depends on the satisfaction of three conditions: (1) that the pH gradient is stable in time; (2) that an electrolyte deficit does not develop within the field, thereby tending to quench the current and/or give rise to local overheating; and (3) that the pH gradient—$d(pH)/dx$—has a low value in the pH region of interest in the actual separation.

Isoelectric focusing is most often practiced in small-scale batch instruments where the fluid is stabilized by either gels or density gradients established by a nonmigrating solute such as sucrose. The capacity of such instruments for product separation is generally limited by the cross-sectional area of the apparatus. Because the apparatus cross-section is limited by the need to dissipate the heat generated by the electric field, larger scale preparative work has been proposed using continuous flow and recycling techniques.

One known technique which comes close to combining high resolution with large quantitative capacity is the recycling isoelectric focusing method disclosed in U.S. Pat. Nos. 4,204,929 and 4,362,612.

Currently known recycling isoelectric focusing (hereinafter "RIEF") techniques involve dividing a fluid containing carrier ampholytes into a plurality of reservoirs and passing the contents of the reservoirs through an isoelectric focusing cell. The isoelectric focusing cell separates the fluids from adjacent reservoirs with ion nonselective permeable membranes which allow interchange of fluid constituents from channel to channel, but which inhibit bulk fluid flow. Electrodes establish an electrical potential transverse to the fluid flow thereby creating a pH gradient between successive channels.

The fluid from each reservoir exiting the isoelectric focusing cell is pumped to the reservoir which feeds the isoelectric focusing cell. A heat exchanger cools the fluid within the reservoirs. As the fluid is pumped into the top of the reservoir, the fluid is directed from the bottom of the reservoir back into the isoelectric focusing cell.

This technique, however, has serious design flaws which preclude its routine use for both research and industrial scale application. The principal design flaw in this technique is that liquid containing material that is semipurified during each circular passage is immediately remixed with the crude starting material in the cooling reservoirs. Thus, the whole process constitutes a continual dilution process in which original crude mixtures in the reservoirs are continually diluted so that final purity is never truly achieved.

The constant remixing of crude and semipurified material in the prior art greatly increases separation time and compromises the resolution of the subcomponents and final purity of the isolated materials. In effect, an asymptotic dilution of contaminants occurs in each separation channel, and therefore a zero contamination level can never be achieved using currently known RIEF techniques.

This constant remixing of semipurified and crude material not only requires very long periods of time for attaining satisfactory degrees of separation, but also requires long periods of time to prefocus the carrier ampholytes into the initial pH gradient. Hence, the overall time required for prefocusing and actual separation is quite long.

Another serious drawback with the current RIEF techniques is the ability to dissipate the joule heat generated during the isoelectric focusing process. Current RIEF techniques cool the processed fluid within the reservoirs. Thus, extreme heating of the fluid sample may occur within the isoelectric focusing cell, irreparably damaging the desired biological sample, before the fluid can be cooled in the reservoirs.

In summary, the burgeoning genetic engineering market in the United States and other Western nations has created an acute need for high resolution protein purification techniques. The manipulation of human and animal genes for numerous hormones, enzymes, and other protein molecules into bacteria, yeast, or mammalian cell liner and the subsequent large-scale production of these proteins has created an acute need for rapid high resolution methods for purification of proteins and other similar biological substances. Although other techniques are frequently used as first or even second step techniques in the purification of these molecules, preparative isoelectric focusing in a narrow pH gradient is an ideal environment in which to do either initial or final stage protein purification.

From the foregoing, it will be appreciated that what is needed in the art are apparatus and methods for isoelectric focusing of amphoteric substances which combine high resolution separation with large quantitative sample capacity.

Additionally, it would be a significant advancement in the art to provide apparatus and methods for recycling isoelectric focusing of amphoteric substances which do not mix semipurified sample with the crude sample.

It would be another advancement in the art to provide apparatus and methods for isoelectric focusing of amphoteric substances which efficiently remove heat generated during the process, thereby permitting increased power input.

It would be a further advancement in the art to provide apparatus and methods for isoelectric focusing of amphoteric substances which rapidly separate the desired substance from accompanying impurities.

It would be yet another advancement in the art to provide apparatus and methods for isoelectric focusing of amphoteric substances which rapidly prefocus to establish a stable pH gradient.

Such methods and apparatus are disclosed and claimed herein.

BRIEF SUMMARY AND OBJECTS OF THE INVENTION

The present invention includes novel apparatus and methods for isoelectric focusing of amphoteric substances within fluids containing carrier ampholytes. The present invention utilizes preparative isoelectric focusing techniques in order to process large volumes of fluid sample. However, fluid which passes through the isoelectric focusing cell is not mixed with the original crude fluid sample. Mixing is avoided by preferably using an alternating or dual reservoir system.

One reservoir of the dual reservoir system supplies the sample fluid to the isoelectric focusing cell and the other reservoir receives the fluid after passing through the focusing cell. After the supply reservoir empties, fluid flow into the isoelectric focusing cell is automatically diverted from the supply reservoir to the receiving reservoir. After appropriate time delay, fluid flow from the isoelectric focusing cell into the receiving reservoir is diverted into the supply reservoir. Fluid flow into and out of each reservoir is automatically alternated after each pass through the isoelectric focusing cell.

The apparatus within the scope of the present invention preferably includes an isoelectric focusing cell having a plurality of inlet ports and a plurality of corresponding outlet ports. The inlet and outlet ports permit fluid to flow into and out of the isoelectric focusing cell along discrete paths. Each inlet and outlet port is preferably coupled to a pair of reservoirs, and each reservoir has a reservoir entrance to allow fluid flow into the reservoir and a reservoir exit to allow fluid flow out of the reservoir.

Fluid flow is preferably alternated into and out of each reservoir of each reservoir pair through use of reservoir inlet and outlet valves. The reservoir inlet and outlet valves preferably operate in response to the fluid level within the reservoir supplying fluid to the isoelectric focusing cell. When the reservoir empties, as measured by the fluid level, the corresponding reservoir outlet valve automatically engages to stop fluid flow from the empty reservoir and to start fluid flow from the full reservoir. After appropriate time delay, the reservoir inlet valve engages to stop fluid flow into the full reservoir and to start fluid flow into the empty reservoir.

The apparatus within the scope of the present invention also preferably has a heat exchanger for removing heat generated by the isoelectric focusing cell. Heat is generated in the isoelectric focusing cell as a direct result of the power input to the isoelectric focusing cell by the electric potential across the focusing cell. The heat exchanger of the present invention may be coupled to the alternating reservoirs thereby cooling the fluid within the reservoirs. However, the heat exchanger is preferably coupled directly to the isoelectric focusing cell. Direct cooling of the isoelectric focusing cell permits greater power input to the focusing cell which results in rapid focusing of both the carrier ampholytes and the fluid sample.

The isoelectric focusing cell preferably includes means for separating the fluid flow into a plurality of focusing cell passageways. Each focusing cell passageway is coupled to corresponding inlet and outlet ports. One proposed method of separating the fluid flow into the focusing cell passageways is with ion non-selective permeable membranes arranged in a substantially parallel configuration which divides the focusing cell into the respective passageways.

Sensors may also be included to sense fluid properties at various locations in the apparatus. For example, pH and temperature sensors provide valuable data regarding status of the separation as well as information useful for efficient separation. Such data may be transmitted to a computer to control, monitor, and record the isoelectric focusing process.

Similarly, the power input to the isoelectric focusing cell may be monitored and may be adjusted by the computer in response to the temperature of the fluid within the focusing cell to maximize the efficiency of the focusing process. Such a technique would permit maximum power input to the isoelectric focusing cell which would produce an acceptable temperature rise. Likewise, the multichannel pump may be controlled by the computer to balance fluid flow through the apparatus with power input and fluid sample separation.

It is, therefore, a primary object of the present invention to provide apparatus and methods for isoelectric focusing of amphoteric substances which combine high resolution separation with large quantitative sample capacity.

Another important object of the present invention is to provide apparatus and methods for isoelectric focusing of amphoteric substances which do not mix semipurified sample with the crude sample.

An additional object of the present invention is to provide apparatus and methods for isoelectric focusing of amphoteric substances which efficiently remove heat generated during the process, thereby permitting increased power input.

Still another important object of the present invention is to provide apparatus and methods for isoelectric focusing of amphoteric substances which rapidly separate the desired substance from accompanying impurities.

A further important object of the present invention is to provide apparatus and methods for isoelectric focusing of amphoteric substances which rapidly prefocus to establish a stable pH gradient.

Other objects and advantages of the present invention will become more fully apparent from the following detailed description and appended claims taken in conjunction with the accompanying drawings, or may be learned from the practice of the invention.

DETAILED DESCRIPTION OF THE PREFERRED EMBODIMENTS

Reference is now made to the drawings wherein like parts are designated with like numerals throughout. As discussed generally above, the present invention is directed to apparatus and methods for isoelectric focusing of amphoteric substances, particularly biological materials. The apparatus of the present invention utilizes preparative isoelectric focusing techniques which eliminate mixing of semipurified and crude amphoteric substances and which provide efficient removal of heat generated during the isoelectric focusing process.

Figure 1:
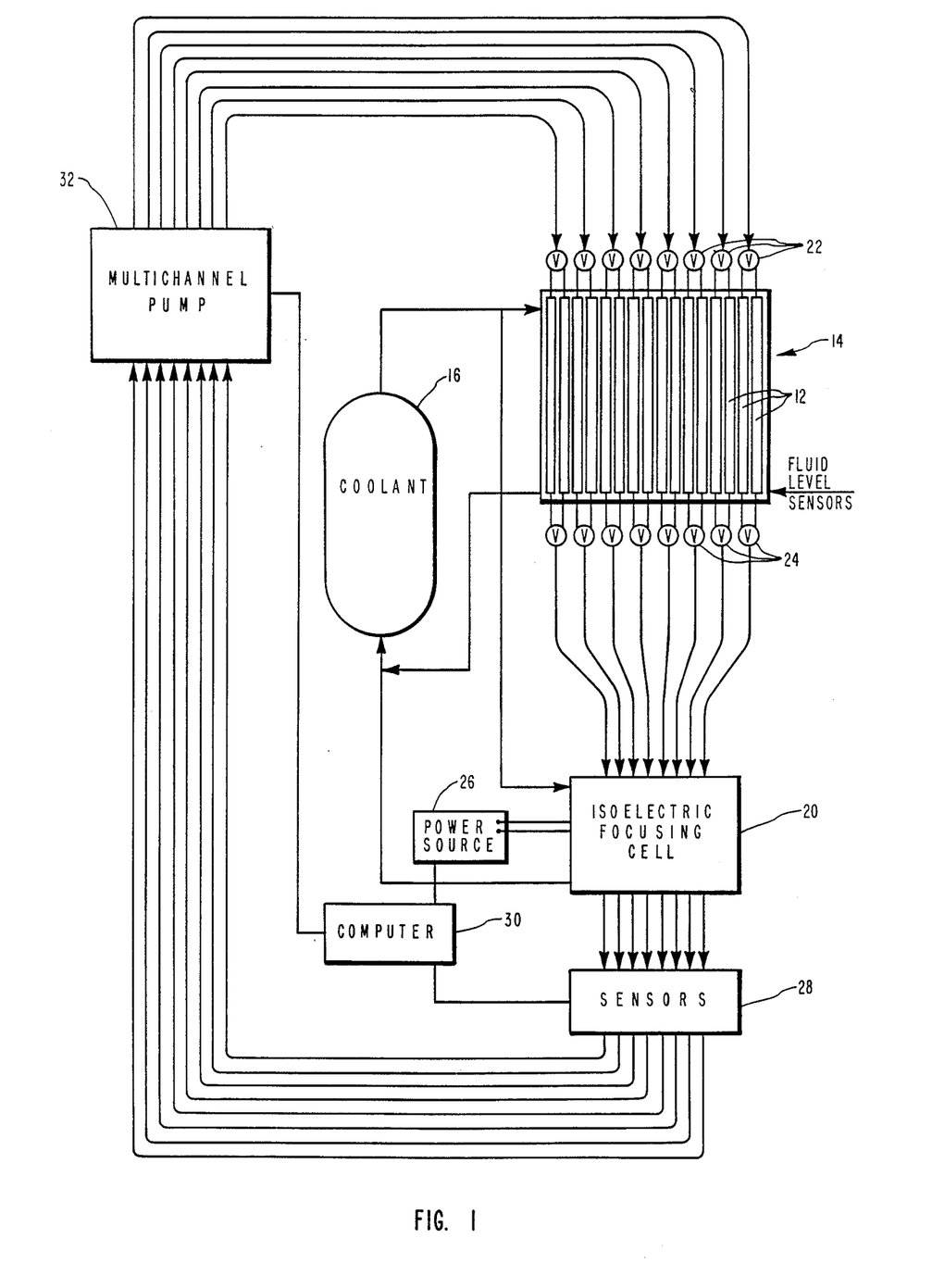
FIG. 1 is a schematic diagram of the recycling isoelectric focusing apparatus within the scope of the present invention.

Referring first to FIG. 1, a schematic view of the overall isoelectric focusing apparatus within the scope of the present invention is illustrated. An important concept of the present invention is eliminating the mixing of semipurified and crude amphoteric substances during recycling. Mixing is avoided by preferably using an alternating or dual reservoir system. Thus, a plurality of reservoirs 12, arranged in pairs, are provided. Reservoirs 12 are located in a reservoir housing 14 which is coupled to a coolant source 16 for cooling the reservoirs within reservoir housing 14.

One reservoir of each reservoir pair supplies the sample fluid to isoelectric focusing cell 20 and the other reservoir of each reservoir pair receives the fluid that has passed through isoelectric focusing cell 20. After the supply reservoir empties, fluid flow into isoelectric focusing cell 20 is automatically diverted from the supply reservoir to the receiving reservoir. Fluid flow from the isoelectric focusing cell into the receiving reservoir is then diverted into the supply reservoir. Thus, fluid flow into and out of each reservoir is automatically alternated after each pass through the isoelectric focusing cell.

Fluid flow is preferably alternated into and out of each reservoir pair through use of reservoir inlet valves 22 and reservoir outlet valves 24. The reservoir inlet and outlet valves preferably operate in response to the fluid level within the reservoir supplying fluid to the isoelectric focusing cell. When the reservoir empties, as measured by fluid level sensors, the corresponding reservoir outlet valve automatically engages to stop fluid flow from the empty reservoir and to start fluid flow from the full reservoir. After appropriate time delay, the reservoir inlet valve engages to stop fluid flow into the full reservoir and to start fluid flow into the empty reservoir.

Also shown in FIG. 1, the apparatus within the scope of the present invention preferably has coolant 16 coupled directly to isoelectric focusing cell 20, thereby providing direct removal of heat generated by the isoelectric focusing cell. The heat is generated by an electric potential across the isoelectric focusing cell. Power source 26 coupled to isoelectric focusing cell 20 provides the necessary electric potential. Direct cooling of the isoelectric focusing cell permits greater power input to the focusing cell which results in rapid focusing and separation of the fluid sample.

Sensors 28 may be provided to measure the temperature, pH or sample concentration in one or more of the outlet channels. Sensors 28 are preferably coupled to computer 80 which may control, monitor, and record the isoelectric focusing process. In addition, the power input to isoelectric focusing cell 20 from power source 26 may be monitored and adjusted by computer 30 in response to the temperature of the fluid within the focusing cell to maximize the efficiency of the focusing process. Similarly, multichannel pump 32 may be controlled by the computer to balance fluid flow through the apparatus with power input and fluid sample separation. Multichannel pump 32 returns the sample fluid exiting isoelectric focusing cell 20 to reservoirs 12.

Figure 2:
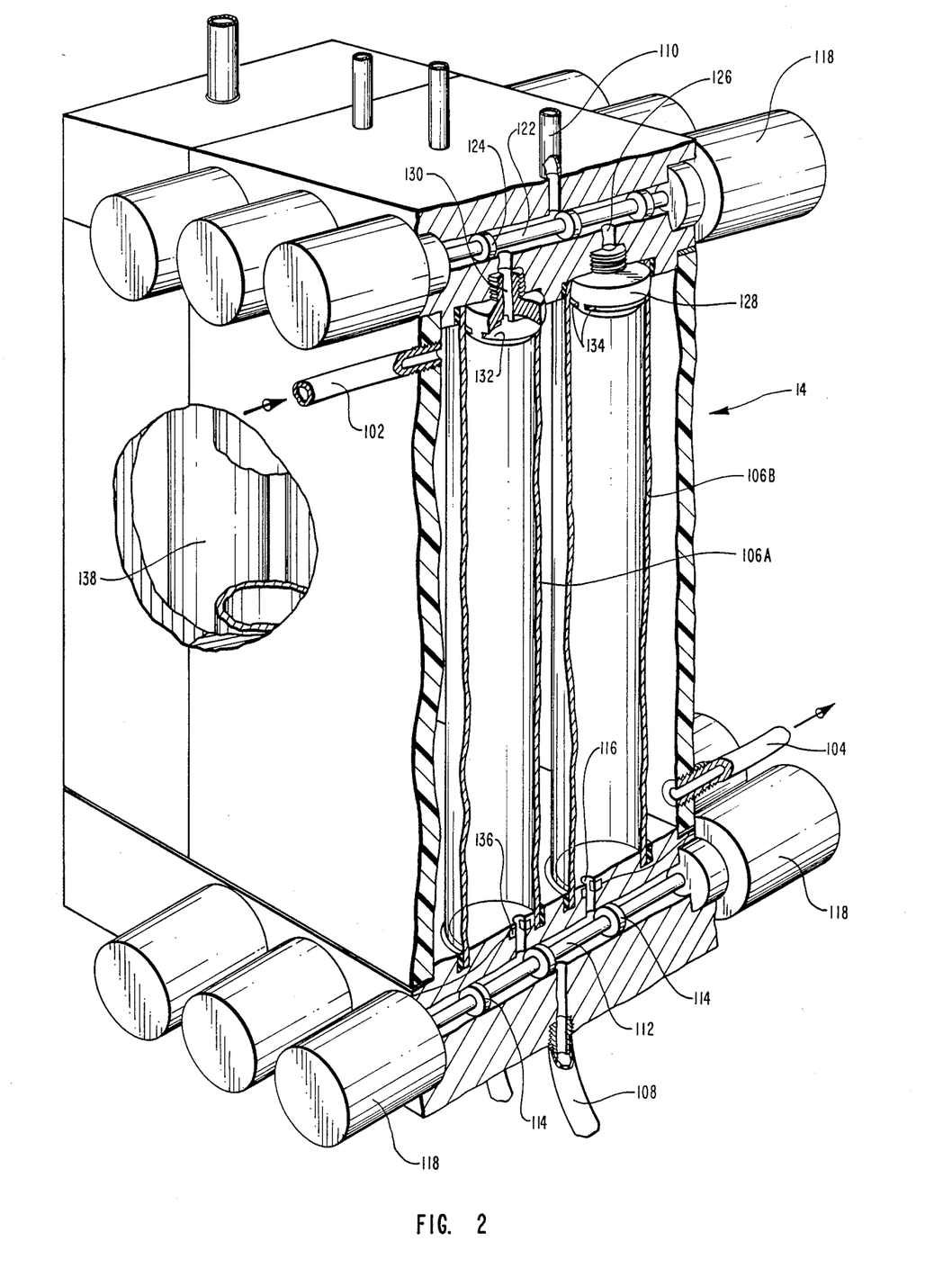
FIG. 2 is a partial cut-away perspective view of a reservoir housing for holding pairs of alternating reservoirs within the scope of the present invention.

Referring now to FIG. 2, a reservoir housing 14 within the scope of the present invention is illustrated in a partial cut-away perspective view. Reservoir housing 14 is designed to accommodate a plurality of reservoirs arranged in pairs. Coolant is circulated around the reservoirs within reservoir housing 14 to remove heat generated during the isoelectric focusing process. Coolant enters reservoir housing 14 through reservoir coolant inlet 102 and exits reservoir housing 14 through reservoir coolant outlet 104.

Each pair of reservoirs, numbered generically as 106A and 106B, is coupled to an inlet channel 108 which directs fluid flow from the reservoir pair to the isoelectric focusing cell. Fluid flowing from the isoelectric focusing cell is directed to a corresponding reservoir pair through a plurality of outlet channels 110. Each outlet channel 110 is coupled to a corresponding reservoir pair.

Fluid flow from each reservoir pair to the corresponding inlet channel 108 is controlled by a reservoir outlet valve. The reservoir outlet valve, as shown in FIG. 2, includes a piston 112 having a series of gaskets 114 which direct fluid flowing from reservoir exit 116 into inlet channel 108. Piston 112 is operated by solenoids 118.

Reservoir inlet valves, which direct fluid flow from each outlet channel 110 into one reservoir of each reservoir pair, have a structure nearly identical to the reservoir outlet valves. Each reservoir inlet valve includes a piston 122 having a series of gaskets 124 which direct fluid flow from outlet channel 110 through reservoir entrance 126 and diffuser 128.

Diffuser 128 causes fluid as it passes through reservoir entrance 126 to flow towards the periphery of each reservoir and descend downward along the reservoir periphery. Diffuser 128 includes a bore 130 which terminates at base 132 defined by two slits 134. As fluid flows through bore 130, it contacts base 132 causing fluid to flow through slits 134 towards the reservoir wall. The fluid then flows down the reservoir wall into the reservoir. Because the fluid flows along the reservoir wall periphery, heat exchange between the sample fluid within the reservoirs and coolant flowing through the reservoir housing is provided.

As discussed above, fluid flow is alternated into and out of each reservoir of each reservoir pair through use of reservoir inlet and outlet valves. The reservoir inlet and outlet valves operate in response to the fluid level within the reservoir supplying fluid to the corresponding inlet channel 108. When the reservoir empties, as measured by fluid level sensors 136, solenoids 118 engage causing piston 112 and gaskets 114 to shift stopping fluid flow from the empty reservoir and starting fluid flow from the full reservoir. After appropriate time delay, the corresponding reservoir inlet valve engages to stop fluid flow into the full reservoir and to start fluid flow into the empty reservoir.

Reservoir housing 14 of FIG. 2 also preferably accommodates two electrode buffer solution reservoirs 138. Buffer solution reservoirs 138 hold the anolyte and catholyte fluids which circulate through the compartment of the isoelectric focusing cell which houses the anode and cathode respectively. Buffer solution reservoirs 138 are not configured in pairs because there is no need to avoid mixing of the buffer solution.

Referring now to FIGS. 3, 4, 5, and 6, one isoelectric focusing cell 20 within the scope of the present invention is illustrated. Isoelectric focusing cell 20 includes a plurality of inlet ports 142 and a plurality of corresponding outlet ports 144. Isoelectric focusing cell 20 preferably includes means for separating the fluid flow into a plurality of focusing cell passageways 146. Each focusing cell passageway is coupled to a corresponding inlet port 142 and outlet port 144.

Electrodes 148 are located within the isoelectric focusing cell in order to create an electric potential across focusing cell passageways 146. Electrodes 148 may be constructed of platinum or any other suitable electrode material used in isoelectric focusing devices.

An electrode buffer solution preferably surrounds each electrode 148. The electrode buffer fluids are generally referred to as the anolyte and catholyte fluids. The catholyte may be a dilute solution of a strong acid, such as sulfuric or phosphoric acid which flows in the cathode or positive electrode compartment 150 as is conventional for isoelectric focusing instruments. The anolyte may be a dilute solution of an alkali, such as sodium hydroxide, in the anode or negative electrode compartment 152, as is conventional for isoelectric focusing instruments. The anolyte and catholyte are matched as closely as possible to the lower and upper pH of the pH gradient, using glycine buffers with pH adjusted using either HCl or NaOH.

Each electrode compartment 150 and 152 is separated from focusing cell passageways 146 by an electrode confining membrane 154. Electrode confining membranes 154 should preferably be ion-selective membranes of the type used in electrodialysis. The positive electrode should be bounded by an anion permeable membrane, and the negative electrode by a cation permeable membrane. Satisfactory ion-selective membranes are manufactured by Sybron Corp.

Isoelectric focusing cell passageways 146 are preferably separated by a plurality of cell separators 156. As shown more clearly in FIG. 4 and FIG. 5, each cell separator includes five components sandwiched together. Each cell separator includes a screen 158, two supports 160, and two gaskets 162.

Figure 4:
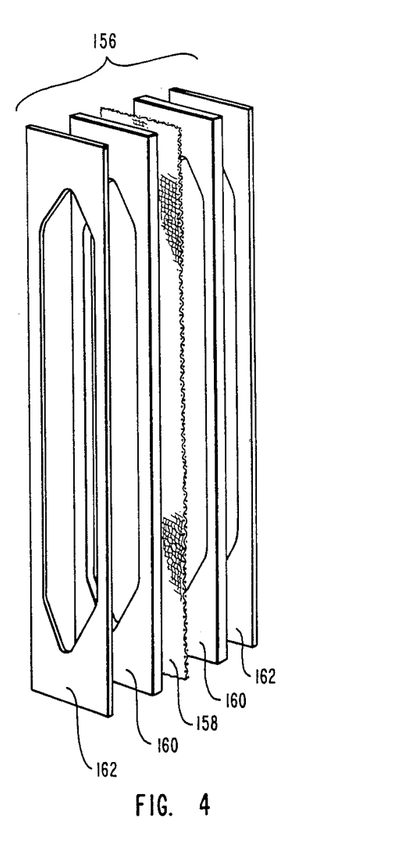
FIG. 4 is an exploded perspective view of a cell separator within the scope of the present invention.
Figure 5:
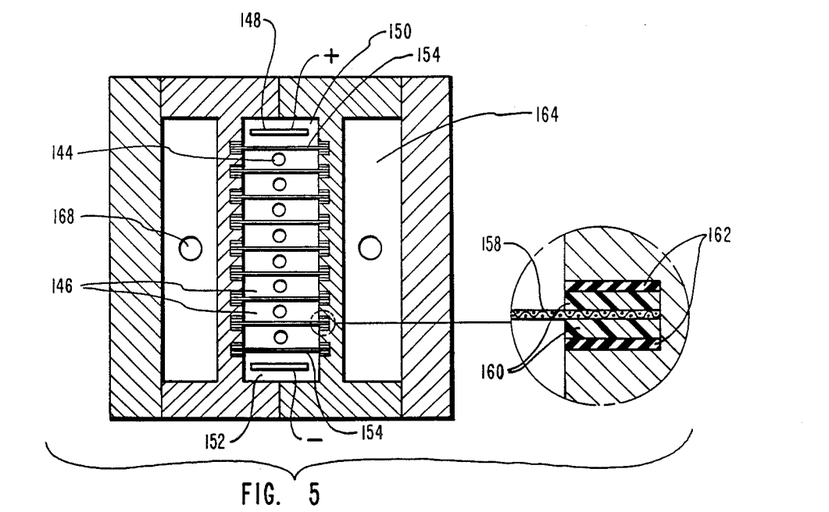
FIG. 5 is a horizontal cross-sectional view of the isoelectric focusing cell of FIG. 3 taken along line 5—5 of FIG. 3.
Figure 6:
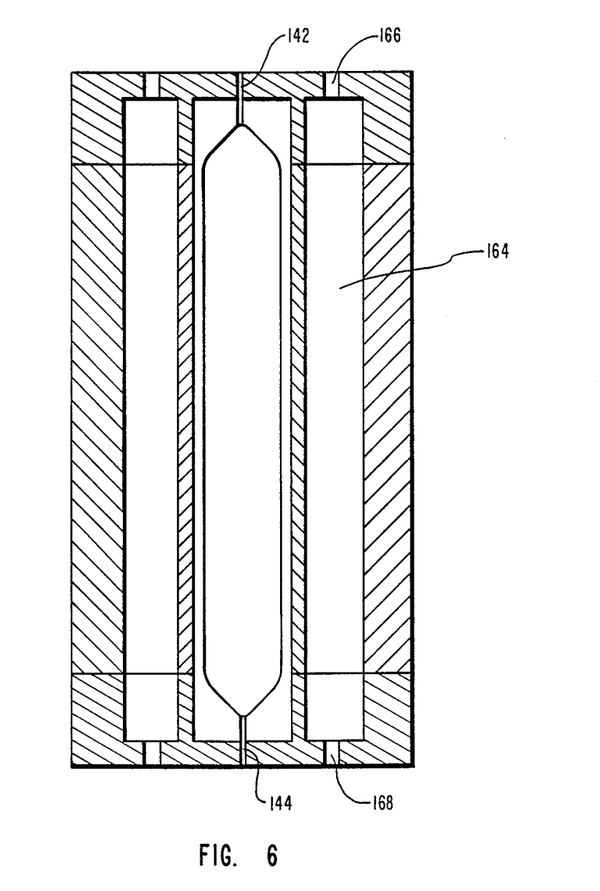
FIG. 6 is a vertical cross-sectional view of the isoelectric focusing cell of FIG. 3 taken along line 6—6 of FIG. 3.

As indicated, supports 160 are generally of a material providing adequate support while being neutral in the electrical field and nonreactive with the ampholytes. One suitable support material is acrylic. Gaskets 162 are preferably constructed of an elastic, nonreactive material such as neoprene. Other suitable materials with sealing capacity and neutrality, such as VITON ® polymers manufactured by DuPont, may also be satisfactory under certain conditions.

Screen 158 is preferably constructed of a biocompatible mesh material such as nylon or teflon. It has been found that a pore size as large as 100 microns is suitable for most amphoteric substances separated by isoelectric focusing.

Biocompatibility is an important characteristic for all components of the isoelectric focusing apparatus within the scope of the present invention. The term biocompatible material used in this specification includes materials which will not denature sensitive proteins being separated or react with or contaminate the proteins.

Generally, the amphoteric substances separated by isoelectric focusing have a molecular weight less than about 500,000. Substances having molecular weights higher than 500,000 typically do not remain in solution long enough to be separated effectively by isoelectric focusing. Thus, the limiting factor in determining suitable amphoteric substances is not pore size of screen 158, but rather molecular weight of the amphoteric substances. As a general rule, the larger the amphoteric substance, the lower the solubility. Nevertheless, solubility can be increased by using suitable solubilizing agents.

It is currently preferred that the solubilizing agents be nonionic and not chemically reactive with either the protein or the ampholytes. Urea, for instance, at 1-5 Molar concentration has been used to enhance solubility without denaturing the proteins being separated. Non-ionic detergents such as Nonidet P-40 and low concentrations (5-10%) butanol have been used successfully. Basically, any nonionic substance can be added to IEF for enhancing solubility. For example, glycerol could be added to enhance the solubility of hydrophobic molecules.

Figure 3:
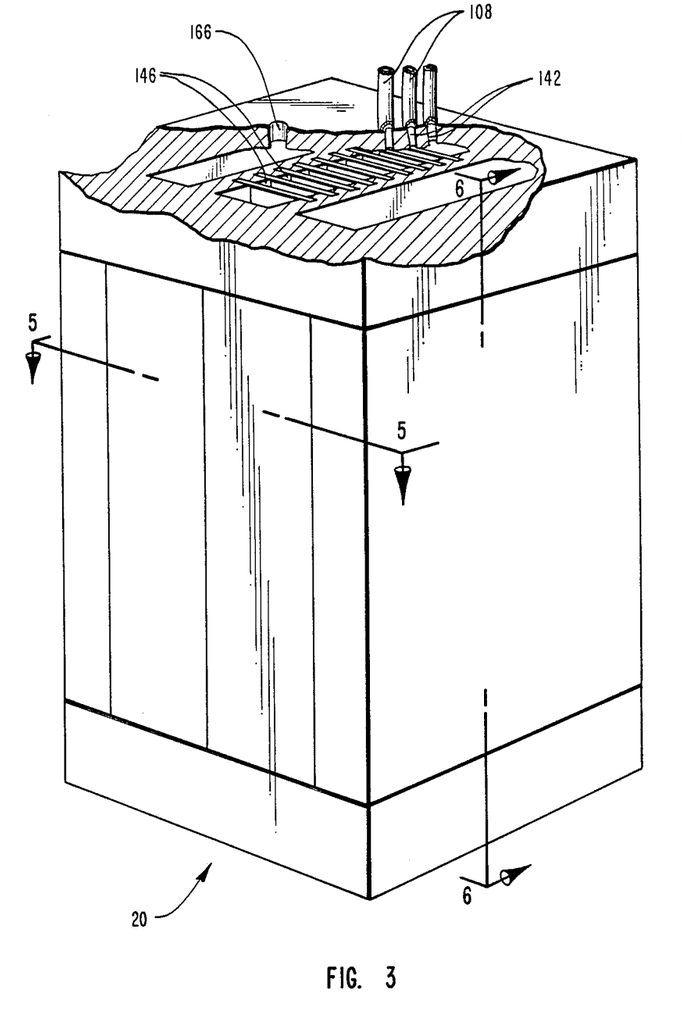
FIG. 3 is a partial cut-away perspective view of an isoelectric focusing cell within the scope of the present invention.

The isoelectric focusing cell within the scope of the present invention preferably includes coolant chambers 164 for direct cooling of fluid flowing through the isoelectric focusing cell. Each coolant chamber 164 has a coolant inlet 166 and a coolant outlet 168. Baffles (not shown) located within coolant chambers 164 create turbulent coolant flow which promotes heat transfer. Coolant flowing through coolant chambers 164 and reservoir housing 10 is preferably maintained around 4 degrees C. One preferred coolant is a 20 percent solution of ethanol to prevent freezing in a refrigeration unit (not shown).

Figure 7:
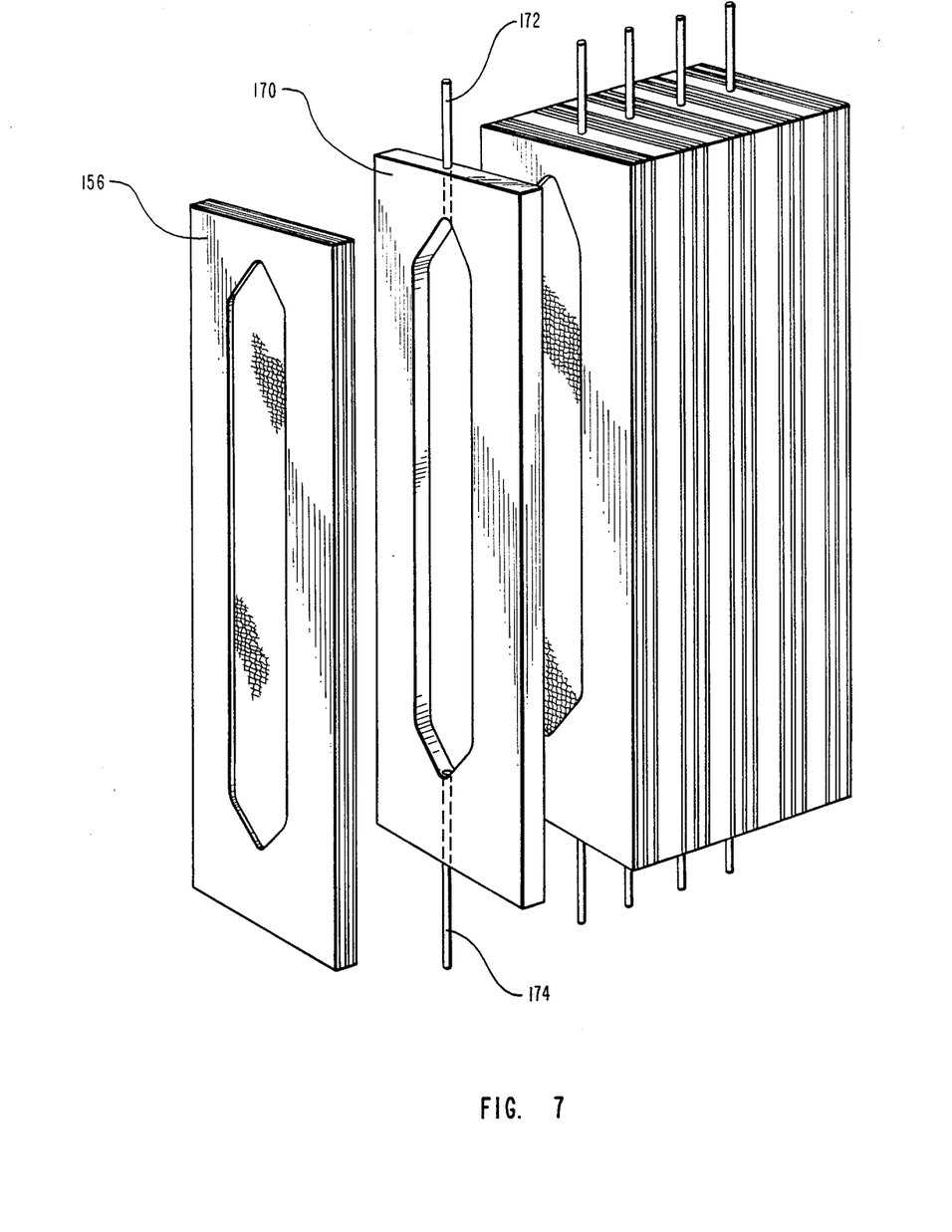
FIG. 7 is an exploded perspective view of another isoelectric focusing cell within the scope of the present invention.

Another isoelectric focusing cell within the scope of the present invention is illustrated in FIG. 7. The isoelectric focusing cell of FIG. 7 may be adjusted to increase or decrease the number of focusing cell passageways in the device. As shown in FIG. 7, individual focusing cell elements 170 may be positioned between alternating focusing cell separators (illustrated in FIG. 4).

Fluid flows into each focusing cell element through an inlet port 172 and exits each focusing cell element through a corresponding outlet port 174. Utilizing the embodiment illustrated in FIG. 7, it is possible to customize the isoelectric focusing cell into the ideal number of focusing cell passageways required to effect the desired separation. A larger number of focusing cell passageways would be useful to separate two or more proteins which are very close to one another in pI (i.e., pI of 6.4 and pI of 6.8). Thus, in a narrow pH gradient made with narrow range ampholytes, a cell with many passageways would help separate the two proteins more efficiently.

Fewer focusing cell passageways would be needed to separate two proteins which have very different pI (i.e., pI of 4 and pI of 8). These would be separated in a wide range gradient and only 3–4 passageways might be necessary for effective separation.

All materials used to construct those portions of the isoelectric focusing apparatus within the scope of the present invention which contact the fluid sample are preferably constructed of biocompatible materials. Biocompatible materials are preferred because most amphoteric substances to be separated are biomaterials such as proteins, peptides, nucleic acids, viruses, and even some living cells. Thus, it is important that all surfaces which contact the amphoteric substances are inert with respect to the amphoteric substances.

For example, upper and lower manifolds of reservoir housing 14 are preferably constructed of ultra-high molecular weight polymer (UHMW 1900, manufactured by High Mowt). Tubing used in the apparatus is preferably constructed of teflon. The isoelectric focusing cell is preferably constructed of acrylic. The reservoir tubes are preferably constructed of pyrex glass. In addition, manual valves (not shown) for filling and draining the isoelectric focusing system are preferably constructed of polycarbonate plastic. As discussed above, all materials used to construct the apparatus which will contact the amphoteric substances are preferably constructed of materials suitable for surgical or medical use.

In a preferred mode of operation using the system described in conjunction with FIG. 1, the solutions are gravity fed from each reservoir pair within reservoir housing 14 to isoelectric focusing cell 20. The isoelectric focusing cell is preferably vertically oriented, i.e., focusing cell separators 156 are in the vertical direction.

The selected buffer solution containing carrier ampholytes suitable for establishment of a stable pH gradient is loaded into one of the two reservoirs of each reservoir pair. A commercially available carrier ampholyte solution is suitable. An electrode buffer solution is loaded into those reservoirs coupled to electrode compartments 150 and 152. These electrode rinses are allowed to flow upward through isoelectric focusing cell 20 to permit venting of gases generated by electrolysis. The preferred direction of flow of the processed fluid is downward through the apparatus.

After equilibration of fluid flow and temperature, electric power is applied from power source 26. Typically, a gradient of about 200 volts to about 250 volts at a constant current is sufficient to cause rapid equilibration. Power input into the focusing cell is maintained relatively constant throughout the separation process. Typical power input is in the range from about 30 watts to about 60 watts. It has been found that the width of the pH gradient significantly affects the time to establish equilibrium. Narrow pH gradients take longer to form than wide pH gradients.

As focusing of the carrier ampholytes occurs, the voltage may be increased up to about 500 to about 600 volts in order to maintain current flow. The maximum power input is limited by the allowable temperature rise in the apparatus due to Joule heating. For this reason, continuous or periodic temperature monitoring is preferred. Typically, a reservoir temperature of 4° C. is maintained. The temperature may increase up to about 10° C. without causing damage to most biomaterials.

In practice, the carrier ampholyte solution is circulated through the apparatus in order to establish a relatively stable pH gradient before the sample material is added. The sample material is then preferably added only to the channel or compartment having a pH relatively close to the pI of the one protein which is desired. It is possible to add the sample material to be focused at the beginning of the operation. Nevertheless, this will cause some of the material to be exposed to extremes of pH in the compartments adjacent to the electrodes. This may damage some pH sensitive biomaterials. In addition, the protein of interest might be ionically altered by exposing it to the whole ampholyte mixture. For example, a protein with acidic pI would be brought into contact with the whole ampholyte mixture if mixed in with the beginning ampholytes prior to running. Some or all of the protein of interest could then bind to some basic ampholytes, thus creating artificial heterogeneity of charge. This might cause all or part of the protein of interest to focus at a different pH than it should. When added to the reservoir containing ampholytes at or very close to the pI of the protein, it never encounters extreme pH ampholytes, thus retaining its inherent charge and pI.

A series of experiments were conducted to detect the difference in mass protein migration between a conventional recirculating isoelectric focusing device ("RIEF") which remixes semipurified fluid with the crude sample fluid and an isoelectric focusing device within the scope of the present invention which alternates fluid flow between pairs of reservoirs. The following examples are intended to be purely exemplary of the use of the invention and should not be considered limiting as to the scope of the present invention.

EXAMPLE 1

In this Example, the difference in mass protein migration between a conventional RIEF device obtained from Ionics, Inc. of Watertown, Mass., and corresponding to the device described in U.S. Pat. Nos. 4,204,929 and 4,362,612 (hereinafter referred to as "mixing device") and an alternating isoelectric focusing device within the scope of the present invention (hereinafter referred to as "alternating device") was determined.

Both the mixing and alternating devices were loaded with 1000 mls of solution containing 1 percent pH specific carrier ampholyte. The solution was prefocused for two hours to establish a pH gradient. Ten (10) milligrams of radioactive labeled Cytochrome C protein was introduced into channel 2 of both devices and allowed to circulate for 15 minutes. At that point, the mixing and alternating devices were turned off and all eight channels from each device were collected individually. A 0.5 ml sample was removed from each channel and counted for the presence of the radioactive labeled protein. The total volume of each channel was measured and the total presence of protein in each channel was calculated using the following formula: counts per minute(cpm)/0.5 ml × 2 × volume = total counts per channel; counts per channel/total counts channel = fraction of total in a given channel.

The results of this Example show that after 15 minutes, 42% of the protein was still in channel 2 of the mixing device, while only 18% of the protein remained in channel 2 of the alternating device. Table I contains the experimental results for Example 1.

| Channel | pH | Volume | cpm/0.5 ml | cpm Total | % cpm |
|---|---|---|---|---|---|
| Mixing Device of the Prior Art: | | | | | |
| 1 | 3.36 | 115 | 264 | 52440 | 2.6 |
| 2 | 4.26 | 133 | 3259 | 857318 | 42.3 |
| 3 | 5.31 | 108 | 809 | 166968 | 8.2 |
| 4 | 6.70 | 128 | 1167 | 289536 | 14.3 |
| 5 | 7.66 | 133 | 1505 | 390754 | 19.3 |
| 6 | 8.47 | 135 | 893 | 231390 | 11.4 |
| 7 | 9.42 | 110 | 211 | 38500 | 1.9 |
| 8 | 9.60 | 136 | 36 | 0 | 0.0 |
| Totals | | 998 | | 2026906 | 100.00 |
| Alternating Device of the Present Invention: | | | | | |
| 1 | 3.60 | 115 | 73 | 8510 | 0.9 |
| 2 | 4.31 | 101 | 933 | 181194 | 18.1 |
| 3 | 5.38 | 107 | 754 | 153652 | 15.4 |
| 4 | 6.81 | 120 | 1490 | 348960 | 35.0 |
| 5 | 7.83 | 139 | 687 | 180978 | 18.1 |
| 6 | 8.24 | 170 | 36 | 0 | 0.0 |
| 7 | 9.28 | 126 | 245 | 52668 | 5.3 |
| 8 | 9.49 | 118 | 343 | 72452 | 7.3 |
| Totals | | 996 | | 998414 | 100.0 |

EXAMPLE 2

In this Example the difference in mass protein migration between a mixing device and an alternating device was determined according to the procedure at Example 1 except that the devices were allowed to focus for 30 minutes after injecting the radio labeled protein before being turned off.

A 0.5 ml sample from each channel was taken and analyzed for the presence of radioactive protein. The results of the 30 minute run times show 13.7% of the protein activity still remaining in channel 2 of the mixing device. The alternating device showed only 3.7% of the protein activity remaining in channel 2. It is believed the 3.7% measured protein activity represents a reading of unbound radioactive iodine and not the presence of the Cytochrome C protein. Table II contains the experimental results for Example 2.

| Channel | pH | Volume | cpm/0.5 ml | cpm Total | % cpm |
|---|---|---|---|---|---|
| Mixing Device: | | | | | |
| 1 | 3.38 | 119 | 158 | 29036 | 1.8 |
| 2 | 4.21 | 123 | 919 | 217218 | 13.7 |
| 3 | 5.21 | 119 | 520 | 115192 | 7.3 |
| 4 | 6.67 | 127 | 698 | 168148 | 10.6 |
| 5 | 7.63 | 123 | 1047 | 248706 | 15.7 |
| 6 | 8.42 | 144 | 1683 | 474336 | 29.9 |
| 7 | 9.36 | 122 | 974 | 228872 | 14.4 |
| 8 | 9.53 | 120 | 471 | 1044000 | 6.6 |
| Totals | | 997 | | 1585908 | 100.00 |
| Alternating Device: | | | | | |
| 1 | 3.37 | 116 | 106 | 16240 | 0.9 |
| 2 | 4.23 | 105 | 352 | 66360 | 3.7 |
| 3 | 5.55 | 124 | 659 | 154504 | 8.6 |
| 4 | 6.95 | 124 | 1150 | 276272 | 15.3 |
| 5 | 7.00 | 126 | 1418 | 348264 | 19.3 |
| 6 | 7.64 | 166 | 2020 | 658688 | 36.5 |
| 7 | 8.36 | 125 | 860 | 206000 | 11.4 |
| 8 | 8.53 | 112 | 393 | 79968 | 4.4 |
| Totals | | 998 | | 1806296 | 100.0 |

EXAMPLE 3

In this Example, the difference in mass protein migration between a mixing device and an alternating device was determined according to the procedure of Example 1, except that the devices were allowed to focus for 45 minutes after injecting the radiolabeled protein before being turned off.

The results of the 45 minute run times show that both devices were virtually void of protein in channel 2. Residual amounts of radiation were detected, which were believed to represent readings of unbound free iodine. Table III contains the experimental results for Example 3.

| Channel | pH | Volume | cpm/0.5 ml | cpm Total | % cpm |
|---|---|---|---|---|---|
| Mixing Device | | | | | |
| 1 | 3.43 | 127 | 132 | 24384 | 1.6 |
| 2 | 4.26 | 109 | 294 | 56244 | 3.7 |
| 3 | 5.21 | 127 | 229 | 49022 | 3.2 |
| 4 | 6.67 | 123 | 371 | 82410 | 5.4 |
| 5 | 7.65 | 140 | 895 | 240520 | 15.9 |
| 6 | 8.44 | 131 | 1433 | 366014 | 24.1 |
| 7 | 9.41 | 133 | 1582 | 411236 | 27.1 |
| 8 | 9.55 | 110 | 1335 | 285780 | 18.9 |
| Totals | | 1000 | | 1515610 | 100.00 |
| Alternating Device: | | | | | |
| 1 | 3.18 | 109 | 90 | 11772 | 0.9 |
| 2 | 3.98 | 117 | 313 | 64818 | 5.0 |
| 3 | 5.22 | 126 | 356 | 80640 | 6.2 |
| 4 | 6.69 | 132 | 692 | 173184 | 13.4 |
| 5 | 7.68 | 121 | 1272 | 299112 | 23.1 |
| 6 | 8.38 | 159 | 1402 | 434388 | 33.6 |
| 7 | 9.32 | 129 | 659 | 160734 | 12.4 |
| 8 | 9.50 | 107 | 355 | 68266 | 5.3 |
| Totals | | 998 | | 1292914 | 100.0 |

The foregoing experimental results demonstrate that the alternating isoelectric focusing device within the scope of the present invention provides significantly more rapid mass migration of protein out of a given pH channel as opposed to conventional recycling isoelectric focusing devices. This is particularly important because protein migration out of a channel is of prime importance when normal operation protocol is observed.

Under normal separation procedure using equipment within the scope of the present invention, the ampholytes are prefocused to establish a pH gradient across the focusing cell passageways. The sample introduced into the prefocused machine is usually a mixture of contaminants and the desired protein. The sample is preferably injected into a channel nearest the isoelectric point of the desired protein. In that channel the desired protein will not migrate, but remain at that point in the pH gradient. The contaminant evacuation from the channel containing the protein of interest is of greatest importance in rapidly obtaining the purified protein. The foregoing examples support the proposition that greater levels of purity can be achieved in a shorter period of time by not remixing the content of a channel.

In practice, the sample fluid from a first reservoir of each reservoir pair is pumped through the isoelectric focusing cell and is returned to the second reservoir of the reservoir pair which is initially empty. Reservoir inlet and outlet valves at the bottom and top of the reservoir housing, preferably in the form of solenoid driven pistons will automatically direct the fluid flow in an alternating fashion between the two reservoirs with the solenoids activated by fluid level sensing devices at the base of each reservoir. As one reservoir empties initially, the other reservoir slowly fills. When the reservoir empties, its fluid level sensor actuates the corresponding reservoir outlet valve for the reservoir pair and closes the reservoir exit for that reservoir and near instantaneously opens the reservoir exit for the other, recently filled, reservoir of the reservoir pair.

After appropriate time delay, the reservoir inlet valve at the top of the reservoir housing switches the returning fluid flow from the isoelectric focusing cell to start filling the empty reservoir. Thus, as fluid sensors inside each reservoir detect fluid levels dropping, they send signals to a controller which activates the solenoids connected to the reservoir inlet and outlet valves connected to each reservoir pair. These reservoir switching actions take place independently for all separation channels. A reservoir pair is preferably coupled to each separation channel.

The number of focusing cell passageways and accompanying reservoir pairs could vary from two (2) to fifty (50), but will normally be in the range from about eight (8) to about twelve (12). Thus, in addition to the reservoirs for anolyte and catholyte solutions, the reservoir housing would include two reservoirs for each separation channel in the isoelectric focusing cell. For the isoelectric focusing cell illustrated in FIG. 2 having eight (8) separation channels, a total of 18 reservoirs would be needed in the reservoir cooling chamber, two (2) reservoirs for each separation channel, and one (1) anolyte reservoir, and one (1) catholyte reservoir.

The basic isoelectric focusing system within the scope of the present invention can include both pH and temperature sensors at the inflow or outflow side of each reservoir, which could be interfaced with a microcomputer for real time monitoring of both pH and temperature of the fluid coming from the focusing cell. The computer may also control the power supply to the focusing cell and also control the flow rate of the multichannel pump which directs the fluid movement in all separation channels.

The computer can also control other valves (not shown) at the inlet and outlet ports to the isoelectric focusing cell which would empty the contents of each reservoir at the end of a separation run into a separate collection vessel. The computer would then activate valves and pumps to refill the reservoirs with starting material from a central holding reservoir and start a new run from the beginning, thereby permitting continuous processing of fluid samples.

From the foregoing, it will be appreciated that the present invention provides apparatus and methods for isoelectric focusing of amphoteric substances which combine high resolution separation with large quantitative sample capacity.

Additionally, it will be appreciated that the present invention provides apparatus and methods for recycling isoelectric focusing of amphoteric substances which do not mix semipurified sample with the crude sample.

Likewise, it will be appreciated that the present invention provides apparatus and methods for isoelectric focusing of amphoteric substances which efficiently remove heat generated during the process, thereby permitting increased power input.

It will also be appreciated that the present invention provides apparatus and methods for isoelectric focusing of amphoteric substances which rapidly separate the desired substance from accompanying impurities.

Finally, it will be appreciated that the present invention provides apparatus and methods for isoelectric focusing of amphoteric substances which rapidly prefocus to establish a stable pH gradient.

It will be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for isoelectric focusing of biological amphoteric substances within a fluid containing buffering components capable of establishing a stable pH gradient in an electric field, the apparatus comprising:
    an isoelectric focusing cell having a plurality of inlet ports and a plurality of corresponding outlet ports;
    a plurality of reservoirs arranged in pairs, each reservoir having a reservoir entrance to allow fluid flow into the reservoir and a reservoir exit to allow fluid flow out of the reservoir; each pair of reservoirs being coupled to a single inlet port of the isoelectric focusing cell and to the corresponding outlet port of the isoelectric focusing cell;
    means for directing fluid flow from each outlet port of the isoelectric focusing cell to the respective reservoir pair;
    means for directing fluid flow from each reservoir pair to the respective inlet port of the isoelectric focusing cell;
    means for alternating the fluid flow into and out of each reservoir of each reservoir pair such that when fluid flows from a first reservoir towards the isoelectric focusing cell, fluid flows from the isoelectric focusing cell towards a second of each reservoir pair such that after the first reservoir empties, fluid is directed to flow from the second reservoir of the respective reservoir pair towards the isoelectric focusing cell and fluid is simultaneously directed to flow into the first reservoir from the isoelectric focusing cell.

2. An apparatus for isoelectric focusing of biological amphoteric substances as defined in claim 1, further comprising a heat exchanger for removing heat generated by the isoelectric focusing cell.

3. An apparatus for isoelectric focusing of biological amphoteric substances as defined in claim 2, wherein the isoelectric focusing cell comprises:
    means for separating the flow of fluid which enters the isoelectric focusing cell into a plurality of parallel focusing cell passageways such that fluid flowing through the inlet ports is channeled to corresponding outlet ports; and
    means for applying an electric potential substantially transverse the plurality of parallel focusing cell passageways.

4. An apparatus for isoelectric focusing of biological amphoteric substances as defined in claim 3, wherein the heat exchanger is coupled to the isoelectric focusing cell.

5. An apparatus for isoelectric focusing of biological amphoteric substances as defined in claim 3, wherein the heat exchanger is coupled to the plurality of reservoirs.

6. An apparatus for isoelectric focusing of biological amphoteric substances as defined in claim 3, further comprising means for sensing the temperature and pH of the fluid within the isoelectric focusing apparatus.

7. An apparatus for isoelectric focusing of biological amphoteric substances as defined in claim 6, further comprising computer means for monitoring and recording data received from the means for sensing the temperature and pH of the fluid within the isoelectric focusing apparatus.

8. An apparatus for isoelectric focusing of biological amphoteric substances as defined in claim 7, wherein the means for sensing the temperature and pH of the fluid is coupled to at least one of the outlet channels.

9. An apparatus for isoelectric focusing of biological amphoteric substances as defined in claim 7, wherein the means for sensing the temperature and pH of the fluid is coupled to at least one of the inlet channels.

10. An apparatus for isoelectric focusing of biological amphoteric substances as defined in claim 3, wherein the means for separating the flow of fluid in the plurality of parallel focusing cell passageways comprise a ion nonselective permeable screen.

11. An apparatus for isoelectric focusing of biological amphoteric substances as defined in claim 10, wherein the ion nonselective permeable screen has a pore size less than about 100 microns.

12. An apparatus for isoelectric focusing of biological amphoteric substances as defined in claim 11, wherein the ion nonselective permeable screen comprises nylon.

13. An apparatus for isoelectric focusing of biological amphoteric substances as defined in claim 11, wherein the ion nonselective permeable screen comprises teflon.

14. An apparatus for isoelectric focusing of biological amphoteric substances as defined in claim 3, wherein the means for directing fluid flow from each outlet port of the isoelectric focusing cell to the respective reservoir pair comprises biocompatible tubing.

15. An apparatus for isoelectric focusing of biological amphoteric substances as defined in claim 3, wherein the means for directing fluid flow from each reservoir pair to the respective inlet port of the isoelectric focusing cell comprises biocompatible tubing.

16. An apparatus for isoelectric focusing of biological amphoteric substances as defined in claim 14, wherein the biocompatible tubing comprises teflon.

17. An apparatus for isoelectric focusing of biological amphoteric substances as defined in claim 15, wherein the biocompatible tubing comprises teflon.

18. An apparatus for isoelectric focusing of biological amphoteric substances as defined in claim wherein the portion of the isoelectric focusing cell which contacts the biological amphoteric substances is constructed of a biocompatible material.

19. An apparatus for isoelectric focusing of biological amphoteric substances as defined in claim 1, wherein the portion of the plurality of reservoirs which contacts the biological amphoteric substances is constructed of a biocompatible material.

20. An apparatus for isoelectric focusing of biological amphoteric substances as defined in claim further comprising a multichannel pump for pumping fluid from each outlet port of the isoelectric focusing cell to the respective reservoir pair.

21. An apparatus for isoelectric focusing of amphoteric substances within a fluid containing buffering components capable of establishing a stable pH gradient in an electric field, the apparatus comprising:
    an isoelectric focusing cell having a plurality of inlet ports and plurality of corresponding outlet ports;
    a plurality of reservoirs arranged in pairs, each reservoir having a reservoir entrance to allow fluid flow into the reservoir and a reservoir exit to allow fluid flow out of the reservoir, each pair of reservoirs corresponding to a single inlet port of the isoelectric focusing cell and a single outlet port of the isoelectric focusing cell;
    a plurality of outlet channels, each coupling an outlet port of the isoelectric focusing cell to the respective reservoir pair;
    a plurality of inlet channels, each coupling the outlet opening of each reservoir pair to the respective inlet port of the isoelectric focusing cell;
    a plurality of reservoir outlet valves coupling the outlet openings of each pair of reservoirs to the corresponding inlet channel, said outlet valves controlling fluid flow out of each pair of reservoirs and into the respective inlet channel, said outlet valves operating independently in response to the fluid level within each pair of reservoirs, such that as the first reservoir empties, its corresponding outlet valve closes the outlet opening of the first reservoir thereby stopping fluid flow from the first reservoir through the inlet channel and opens the corresponding outlet opening of the second reservoir, thereby initiating fluid flow from the second reservoir to the focusing cell;
    a plurality of reservoir inlet valves coupling the inlet openings of each pair of reservoirs to the corresponding outlet channel, said inlet valves controlling fluid flow into each pair of reservoirs, said inlet valves operating in harmony with said outlet valves such that as the outlet valve for each pair of reservoirs switch fluid flow from the first reservoir to the second reservoir, said inlet valves close the inlet opening into the second reservoir and to open the inlet opening into the first reservoir;
a multichannel pump for pumping the fluid in said outlet channels; and
a heat exchanger for removing heat generated by the isoelectric focusing cell.

22. An apparatus for isoelectric focusing of amphoteric substances as defined in claim 21, wherein the isoelectric focusing cell comprises:
means for separating the flow of fluid which enters the isoelectric focusing cell into a plurality of parallel focusing cell passageways such that fluid flowing through the inlet ports is channeled to corresponding outlet ports; and
means for applying an electric potential substantially transverse the plurality of parallel focusing cell passageways.

23. An apparatus for isoelectric focusing of amphoteric substances as defined in claim 22, wherein the heat exchanger is coupled to the isoelectric focusing cell.

24. An apparatus for isoelectric focusing of amphoteric substances as defined in claim 22, wherein the heat exchanger is coupled to the plurality of reservoirs.

25. An apparatus for isoelectric focusing of amphoteric substances as defined in claim 22, further comprising means for sensing the temperature and pH of the fluid within the isoelectric focusing apparatus.

26. An apparatus for isoelectric focusing of amphoteric substances as defined in claim 25, further comprising computer means for monitoring and recording data received from the means for sensing the temperature and pH of the fluid within the isoelectric focusing apparatus.

27. An apparatus for isoelectric focusing of amphoteric substances as defined in claim 25, wherein the means for sensing the temperature and pH of the fluid is coupled to at least one of the outlet channels.

28. An apparatus for isoelectric focusing of biological amphoteric substances as defined in claim 25, wherein the means for sensing the temperature and pH of the fluid is coupled to at least one of the inlet channels.

29. An apparatus for isoelectric focusing of biological amphoteric substances as defined in claim 22, wherein the means for separating the flow of fluid into the plurality of parallel focusing cell passageways comprise a ion nonselective permeable screen.

30. An apparatus for isoelectric focusing of amphoteric substances as defined in claim 22, wherein the ion nonselective permeable screen has a pore size less than about 100 microns.

31. An apparatus for isoelectric focusing of amphoteric substances as defined in claim 22, wherein the ion nonselective permeable screen comprises nylon.

32. An apparatus for isoelectric focusing of amphoteric substances as defined in claim 22, wherein the ion nonselective permeable screen comprises teflon.

33. An apparatus for isoelectric focusing of amphoteric substances as defined in claim 21, wherein the means for directing fluid flow from each outlet port of the isoelectric focusing cell to the respective reservoir pair comprises biocompatible tubing.

34. An apparatus for isoelectric focusing of amphoteric substances as defined in claim 22, wherein the means for directing fluid flow from each reservoir pair to the respective inlet port of the isoelectric focusing cell comprises biocompatible tubing.

35. An apparatus for isoelectric focusing of amphoteric substances as defined in claim 33, wherein the biocompatible tubing comprises teflon.

36. An apparatus for isoelectric focusing of amphoteric substances as defined in claim 34, wherein the biocompatible tubing comprises teflon.

37. An apparatus for isoelectric focusing of amphoteric substances as defined in claim 21, wherein the portion of the isoelectric focusing cell which contacts the amphoteric substances is constructed of a biocompatible material.

38. An apparatus for isoelectric focusing of amphoteric substances as defined in claim 21, wherein the portion of the plurality of reservoirs which contacts the amphoteric substances is constructed of a biocompatible material.

39. An apparatus for isoelectric focusing of biological amphoteric substances within a fluid containing buffering components capable of establishing a stable pH gradient in an electric field, the apparatus comprising:
an isoelectric focusing cell constructed from a plurality of parallel focusing cell elements separated by a plurality of focusing cell separators, each said focusing cell element having a respective inlet port and a corresponding outlet port, each said focusing cell element having a fluid passageway therein;
a plurality of reservoirs arranged in pairs, each reservoir having a reservoir entrance to allow fluid flow into the reservoir and a reservoir exit to allow fluid flow out of the reservoir, each pair of reservoirs being coupled to the inlet port of a corresponding focusing cell element and to the outlet port of the corresponding focusing cell element;
means for directing fluid flow from each outlet port of the focusing cell elements to the respective reservoir pair;
means for directing fluid flow from each reservoir pair to the respective inlet ports of the focusing cell elements;
means for alternating the fluid flow into and out of each reservoir of each reservoir pair such that when fluid flows from a first reservoir towards the isoelectric focusing cell, fluid flows from the isoelectric focusing cell towards a second of each reservoir pair such that after the first reservoir empties, fluid is directed to flow from the second reservoir of the respective reservoir pair towards the isoelectric focusing cell and fluid is simultaneously directed to flow into the first reservoir from the isoelectric focusing cell.

40. An apparatus for isoelectric focusing of biological amphoteric substances as defined in claim 39, further comprising a heat exchanger for removing heat generated by the isoelectric focusing cell.

41. An apparatus for isoelectric focusing of biological amphoteric substances as defined in claim 40, wherein the isoelectric focusing cell further comprises means for applying an electric potential substantially transverse the plurality of parallel focusing cell elements.

42. An apparatus for isoelectric focusing of biological amphoteric substances as defined in claim 41, wherein the heat exchanger is coupled to the isoelectric focusing cell.

43. An apparatus for isoelectric focusing of biological amphoteric substances as defined in claim 41, wherein the heat exchanger is coupled to the plurality of reservoirs.

44. An apparatus for isoelectric focusing of biological amphoteric substances as defined in claim 41, further comprising means for sensing the temperature and pH of the fluid within the isoelectric focusing apparatus.

45. An apparatus for isoelectric focusing of biological amphoteric substances as defined in claim 44, further comprising computer means for monitoring and recording data received from the means for sensing the temperature and pH of the fluid within the isoelectric focusing apparatus.

46. An apparatus for isoelectric focusing of biological amphoteric substances as defined in claim 45, wherein the means for sensing the temperature and pH of the fluid is coupled to at least one of the outlet channels.

47. An apparatus for isoelectric focusing of biological amphoteric substances as defined in claim 45, wherein the means for sensing the temperature and pH of the fluid is coupled to at least one of the inlet channels.

48. An apparatus for isoelectric focusing of biological amphoteric substances as defined in claim 41, wherein the means for separating the flow of fluid in the plurality of parallel focusing cell passageways comprise a ion nonselective permeable screen.

49. An apparatus for isoelectric focusing of biological amphoteric substances as defined in claim 48, wherein the ion nonselective permeable screen has a pore size less than about 100 microns.

50. An apparatus for isoelectric focusing of biological amphoteric substances as defined in claim 49, wherein the ion nonselective permeable screen comprises nylon.

51. An apparatus for isoelectric focusing of biological amphoteric substances as defined in claim 49, wherein the ion nonselective permeable screen comprises teflon.

52. An apparatus for isoelectric focusing of biological amphoteric substances as defined in claim 41, wherein the means for directing fluid flow from each outlet port of the isoelectric focusing cell to the respective reservoir pair comprises biocompatible tubing.

53. An apparatus for isoelectric focusing of biological amphoteric substances as defined in claim 41, wherein the means for directing fluid flow from each reservoir pair to the respective inlet port of the isoelectric focusing cell comprises biocompatible tubing.

54. An apparatus for isoelectric focusing of biological amphoteric substances as defined in claim 52, wherein the biocompatible tubing comprises teflon.

55. An apparatus for isoelectric focusing of biological amphoteric substances as defined in claim 53, wherein the biocompatible tubing comprises teflon.

56. An apparatus for isoelectric focusing of biological amphoteric substances as defined in claim 39, wherein the plurality of focusing cell elements which contact the biological amphoteric substances are constructed of a biocompatible material.

57. An apparatus for isoelectric focusing of biological amphoteric substances as defined in claim 39, wherein the plurality of focusing cell separators which contact the biological amphoteric substances are constructed of a biocompatible material.

58. An apparatus for isoelectric focusing of biological amphoteric substances as defined in claim 39, wherein the portion of the plurality of reservoirs which contacts the biological amphoteric substances is constructed of a biocompatible material.

59. An apparatus for isoelectric focusing of biological amphoteric substances as defined in claim 39, further comprising a multichannel pump for pumping fluid from each outlet port of the isoelectric focusing cell to the respective reservoir pair.

60. A method for isoelectric focusing of amphoteric substances comprising the steps of:
passing fluid containing buffering components into an isoelectric focusing cell having a plurality of inlet ports, a plurality of corresponding outlet ports, and a plurality of isoelectric focusing cell passageways coupling each inlet port with a respective outlet port, said fluid being capable of establishing a stable pH gradient in an electric field;
applying an electric potential in a direction substantially transverse to the direction of fluid flow through the isoelectric focusing cell passageways, thereby establishing a stable pH gradient across the isoelectric focusing cell passageways;
introducing an amphoteric substance to be analyzed into the fluid such that the amphoteric substance passes into the isoelectric focusing cell;
circulating fluid exiting the isoelectric focusing cell to a plurality of reservoirs arranged in pairs such that each outlet port of the isoelectric focusing cell is coupled to a pair of reservoirs and such that each pair of reservoirs is coupled to a corresponding inlet port of the isoelectric focusing cell;
alternating the fluid flow into and out of each reservoir of each reservoir pair such that when fluid flows from a first reservoir into a respective inlet port of the isoelectric focusing cell, fluid flows from a corresponding outlet port of the isoelectric focusing cell into a second of each reservoir pair such that after the first reservoir empties, fluid is directed to flow from the second reservoir of the respective reservoir pair into the respective inlet port and fluid is simultaneously directed to flow into the first reservoir from the respective outlet port.

61. A method for isoelectric focusing of amphoteric substances as defined in claim 60, further comprising the step of cooling the isoelectric focusing cell while the fluid passes through the isoelectric focusing cell.

62. A method for isoelectric focusing of amphoteric substances as defined in claim 61, wherein the step of cooling the isoelectric focusing cell comprises passing a coolant through the isoelectric focusing cell.

63. A method for isoelectric focusing of amphoteric substances as defined in claim 60, wherein the amphoteric substance is a biological substance.

64. A method for isoelectric focusing of amphoteric substances as defined in claim 60, further comprising the step of cooling the plurality of reservoirs by flowing a coolant around the reservoirs.

65. A method for isoelectric focusing of amphoteric substances as defined in claim 60, further comprising the step of sensing the pH and temperature of the fluid exiting the isoelectric focusing cell.

66. A method for isoelectric focusing of amphoteric substances as defined in claim 65, further comprising the step of monitoring and recording the pH and temperature of the fluid exiting the isoelectric focusing cell.

67. A method for isoelectric focusing of amphoteric substances as defined in claim 66, further comprising the step of controlling the electric potential applied to the isoelectric focusing cell in response to the temperature of the fluid exiting the isoelectric focusing cell.

68. A method for isoelectric focusing of biological amphoteric substances comprising the steps of:

passing fluid containing buffering components into an isoelectric focusing cell having a plurality of inlet ports, a plurality of corresponding outlet ports, and a plurality of parallel isoelectric focusing cell passageways coupling each inlet port with a respective outlet port, said isoelectric focusing cell passageways being separated by ion nonselective permeable screens, said fluid being capable of establishing a stable pH gradient in an electric field;

applying an electric potential in a direction substantially transverse to the direction of fluid flow through the isoelectric focusing cell, thereby establishing a stable pH gradient across the isoelectric focusing cell passageways;

introducing an amphoteric substance to be analyzed into the fluid such that the amphoteric substance passes into the isoelectric focusing cell;

circulating the fluid exiting the isoelectric focusing cell through a plurality of outlet channels coupled to corresponding outlet ports of the isoelectric focusing cell, each outlet channel being coupled to a pair of reservoirs, and each pair of reservoirs being coupled to an inlet channel coupled to corresponding inlet ports of the isoelectric focusing cell; and alternating the fluid flow into and out of each reservoir of each reservoir pair such that when fluid flows from a first reservoir into a respective inlet channel, fluid flows from a corresponding outlet channel into a second of each reservoir pair, such that after the first reservoir empties, fluid is directed to flow from the second reservoir of the respective reservoir pair into the respective inlet channel and fluid is simultaneously directed to flow into the first reservoir from the respective outlet channel.

69. A method for isoelectric focusing of amphoteric substances as defined in claim 68, further comprising the step of cooling the isoelectric focusing cell while the fluid passes through the isoelectric focusing cell.

70. A method for isoelectric focusing of amphoteric substances as defined in claim 69, wherein the step of cooling the isoelectric focusing cell comprises passing a coolant through the isoelectric focusing cell.

71. A method for isoelectric focusing of amphoteric substances as defined in claim 68, further comprising the step of cooling the plurality of reservoirs.

72. A method for isoelectric focusing of amphoteric substances as defined in claim 68, further comprising the step of sensing the pH and temperature of the fluid exiting the isoelectric focusing cell.

73. A method for isoelectric focusing of amphoteric substances as defined in claim 68, further comprising the step of monitoring and recording the pH and temperature of the fluid exiting the isoelectric focusing cell.

74. A method for isoelectric focusing of amphoteric substances as defined in claim 73, further comprising the step of controlling the electric potential applied to the isoelectric focusing cell in response to the temperature of the fluid exiting the isoelectric focusing cell.

* * * * *

UNITED STATES PATENT AND TRADEMARK OFFICE
CERTIFICATE OF CORRECTION

PATENT NO. : 4,963,236

Page 1 of 2

DATED : October 16, 1990

INVENTOR(S) : L. SCOTT RODKEY

It is certified that error appears in the above-identified patent and that said Letters Patent is hereby corrected as shown below:

Column 14, line 56, ";" should be --,--
Column 15, line 53, "a ion" should be --an ion--
Column 16, line 25, after "claim" insert --1,--
Column 17, lines 46-47, "a ion" should be --an ion--
Column 19, line 22, "a ion" should be --an ion--
Abstract, lines 17-18, after "reservoir" insert --, the--
Abstract, line 20, replace "Near" with --Nearly--
Column 11, line 35, insert the following:

--Table I

Solution of 1000 ml 1% w/v ampholytes with 2 hour prefocus
10 mg. Cytochrome C + 500 uL I-125 labeled Cytochrome C
into channel 2 with a 15 minute run time.--
Mixing Device of the Prior Art:

Column 12, line 6, insert the following:

--Table II

Solution of 1000 ml 1% w/v ampholytes with 2 hour prefocus
10 mg. Cytochrome C + 500 uL I-125 labeled Cytochrome C
into channel 2 with a 30 minute run time.--
Mixing Device:

UNITED STATES PATENT AND TRADEMARK OFFICE
CERTIFICATE OF CORRECTION

PATENT NO. : 4,963,236

DATED : October 16, 1990

INVENTOR(S) : L. SCOTT RODKEY

It is certified that error appears in the above-identified patent and that said Letters Patent is hereby corrected as shown below:

Column 12, line 42, insert the following:

--Table III

Solution of 1000 ml 1% w/v ampholytes with 2 hour prefocus 10 mg. Cytochrome C + 500 uL I-125 labeled Cytochrome C into channel 2, with a 45 minute run time.--

Mixing Device

Column 13, line 12, "remain" should be --remains--

Signed and Sealed this

Twenty-second Day of September, 1992

Attest:

DOUGLAS B. COMER

Attesting Officer  Acting Commissioner of Patents and Trademarks